US006451359B1

(12) United States Patent
Nsofor

(10) Patent No.: US 6,451,359 B1
(45) Date of Patent: Sep. 17, 2002

(54) SOY BEVERAGE AND RELATED METHOD OF MANUFACTURE

(75) Inventor: Leslie M. Nsofor, Lansing, MI (US)

(73) Assignee: Soy Ultima, L.L.C., East Lansing, MI (US)

( * ) Notice: Subject to any disclaimer, the term of this patent is extended or adjusted under 35 U.S.C. 154(b) by 0 days.

(21) Appl. No.: 09/634,933

(22) Filed: Aug. 8, 2000

(51) Int. Cl.$^7$ .............................. A23L 1/20; A23L 2/38; A23J 1/14
(52) U.S. Cl. .................... 426/46; 426/656; 426/634; 426/598
(58) Field of Search ................... 426/634, 656, 426/46, 598

(56) References Cited

U.S. PATENT DOCUMENTS 4,041,187 A   8/1977   Nelson et al.

FOREIGN PATENT DOCUMENTS

EP   1120047   8/1999

OTHER PUBLICATIONS

Nsofor, L.M. Suitability of ultrafiltered soybean extract for developing evaporated cow milk analogue. 1996; 33:322–325, J. Fd. Sci. Technol.

Nsofor, L.M. Development of soybean–based milkshake analogue: final stage. 1995; Research report submitted to Federal University of Technology, Owerri, Nigeria.

Nsofor, L.M. & I. Ikegwuoha. Preliminary evaluation of polysaccharide hydrolysis during incubation of mashed sprouted soybeans. 1994; (Unpublished).

Nsofor, L.M. et al. Storage stability of concentrated soymilk; evaluation of cowmilk concentrate and salts' addition and soybean acid—steeping. 1993; 28;499–504, Inter. J. Fd. Sci. Technol.

Nsofor, L.M. Evaporated cow's milk analog development: stability of ultrafiltered extract of hydrolyzed soybeans. 1992; Research proposal submitted to International Foundation for Science, Stockholk, Sweden.

Nsofor, L.M. & O. Maduako. Stabilized soymilk for ambient tropical storage: a preliminary report. 1992; 25:573–576, Inter. J. Fd. Sci. Technol.

Nsofor, L.M. & K.B. Anyanwu. Development and evaluation of concentrated soy beverages. 1992(b) 29: 331–332, J. Fd. Sci. Technol.

Nsofor, L.M. & K.B.Anyanwu. Effect of heat processing on refrigerated shelf–life of concentrated soymilk beverage. 1992(a); 29;40–44, J. Fd. Sci. Technol.

Nsofor, L.M. et al. Storage stability and chemical properties of soymilk concentrates developed from sprouted soybeans. 1997; 477–482, J. Fd. Sci. Technol.

Nsofor, L.M. & C.M. Osuji. Stability, rheology and chemical properties of soymilk concentrates developed from sprouted soybeans. 1997; 34:33–40, J. Fd. Sci. Technol.

Nsofor, L.M. & B.N. Azubike. Feasibility of Shelf–stable soymilk from enzyme–hydrolyzed soybean flour. Oct. 1996. Paper presented at 5th Annual Conference of Nigerian Society for Biological Conservation.

*Primary Examiner*—Anthony J Weier
(74) *Attorney, Agent, or Firm*—Warner Norcross & Judd LLP

(57) ABSTRACT

A process for producing a stabilized soy beverage from dehulled whole soybeans partially hydrolyzed with enzymes. The process includes: providing whole soybeans; hydrating the soybeans to activate endogenous enzymes within the soybeans; dehulling the soybeans; hydrolyzing the proteins within the dehulled soybean cotyledons by incubating the cotyledons at elevated temperatures; gelatinizing the incubated cotyledons to induce coagulation of the soybean polysaccharides; milling the gelatinized cotyledons into a slurry; hydrolyzing the polysaccharides of the cotyledons, aided by the addition of cellulase; deodorizing the slurry to form a hydrolyzed soy base; mixing sweeteners, flavoring, and solubilization aids with the hydrolyzed soy base; homogenizing the hydrolyzed soy base; and heat treating the hydrolyzed soy base to form a soy beverage.

26 Claims, No Drawings

SOY BEVERAGE AND RELATED METHOD OF MANUFACTURE

BACKGROUND OF THE INVENTION

The present invention relates to soy products, and more particularly to stabilized soy beverages manufactured from dehulled whole soybeans.

Soybean or legume based food products are known for their high protein content and other health benefits such as the reduction of blood cholesterol and incidents of osteoporosis. The manufacture of soy beverage products presents a variety of distinct problems due to the chemical composition of the soybeans. For example, typical whole soy beverages usually have a chalky or fibrous texture due to the complex carbohydrates present in the soybean cotyledons and hulls. Further, soy beverages are typically plagued with a "beany" flavor caused by enzyme activity, in particular, lipoxygenase activity, that results from the cell tissue of soybean cotyledons being disrupted in the presence of moisture and oxygen.

In conventional soy beverage manufacturing processes, these problems have been addressed. Typical soymilk beverages include a combination of water and soymilk concentrate produced from a process whereby whole soybeans are dehulled and blanched. To reduce the chalky texture of the soy beverage, the soybeans are dry-dehulled prior to processing. Dry-dehulling is the industrial process whereby the soybeans are heated so that the hull is separated from the cotyledon. The soybean hull is then physically cracked and subsequently separated from the cotyledon. Alternatively, the chalky texture may be reduced by extracting the soybeans. Conventional extraction includes crushing the whole soybeans in water and pressing the resultant slurry to squeeze out a soybean liquid. To address the "beany" flavor of the resultant soy beverage, the soybeans are blanched—that is, boiled or steamed at very high temperatures. Blanching inactivates the lipoxygenase enzyme present in the soybean and eliminates the possibility of the soybean developing the "beany" flavor during subsequent processing. During the blanching step, however, the soy proteins are substantially denatured whereby solubilization of the soy proteins is inhibited.

Although manufacture of prior art soy beverages removes the chalky texture and "beany" flavor of the beverage, a distinct problem arises during storage of the beverage in containers. In particular, the beverage is extremely unstable. The beverage separates into at least two layers; a clumpy colloidal (particle) phase at the base of the container, and a free whey water phase at the top of the container. Accordingly, the beverage becomes unattractive in this separated, clumpy-looking state. Further, consumers must vigorously shake the container to recombine the colloidal phase and water phase before consuming the beverage to avoid an unpleasant texture. In the prior art, it was thought that the denaturation of the protein during the application of heat to inactivate the lipoxygenase was the cause of the colloidal separation.

To eliminate the unattractive appearance of prior art soy beverages, manufacturers conventionally package the beverage in opaque containers such as laminated paper boxes or colored plastic bottles. Although this conceals the separation of the colloidal phase and the water phase, the soy beverage still must be shaken to uniformly distribute the soybean particles in the water phase and prevent clumping when the beverage is poured from the storage container.

Manufacturers of soy beverages of the prior art have also addressed soy beverage instability by isolating soy nutraceuticals, such as particular soy proteins and soy isoflavones from whole soybeans, and putting the nutraceuticals alone in a beverage. Although the resultant soy beverage is somewhat stable, only a select few soy nutraceuticals are present therein. Thus, consumers obtain a limited number of soy nutraceuticals when they consume these soy beverages rather than the synergistic composition of all the soybean's nutraceuticals.

SUMMARY OF THE INVENTION

The aforementioned problems are overcome in the present invention for manufacturing a stabilized soy beverage from dehulled-whole soybeans that are hydrolyzed with enzymes. The soy beverage produced from the inventive process exhibits stability for extended periods of storage, absence of a "beany" flavor and lack of a chalky texture. In particular, during storage, the colloidal and water phases of the soy beverage do not separate, even for extended periods of storage. Before consuming the soy beverage, agitation of the soy beverage is unnecessary, as the colloidal and water phases do not separate in storage. Further, the soy beverage of the present invention is created from dehulled-whole soybeans; therefore all of the beneficial nutraceuticals of the dehulled-whole soybeans, such as soy proteins, isoflavones, trypsin inhibitors, saponins, phytates, phosphatides, fiber, omega-3-fatty acids and vitamin E, to name a few, are present in the resultant beverage.

It has been discovered that colloidal separation of soy beverage during storage is caused by the binding of proteins and carbohydrates present in the whole soybeans used to manufacture the beverage. Once the proteins and carbohydrates bind together, the large macro molecules formed thereby tend to clump together and separate and/or precipitate out from the liquid phase. According to this discovery, the process of the present invention enzymatically hydrolyzes the soy proteins and soy carbohydrates to extensively inhibit binding to one another and subsequent colloidal separation. The resultant product of this process is a hydrolyzed soy base.

More particularly, the process of the present invention used to manufacture the hydrolyzed soy base includes the steps of: providing whole soybeans that include carbohydrates and proteins; hydrolyzing the proteins and hydrolyzing the carbohydrates so that the proteins and carbohydrates do not bind to form colloidal masses. In the preferred embodiment of the present invention, the process of manufacturing a hydrolyzed soy base includes the steps of: providing whole soybeans; soaking and preliminarily incubating the whole soybeans so that endogenous enzymes of the soybean are brought to a potentially active state; dehulling the soaked soybeans and separating the wet hulls from the cotyledons; incubating the cotyledons at a temperature so that enzymes present in the soybean begin to hydrolyze the soy protein and carbohydrates; gelatinizing the partially hydrolyzed complex polysaccharides in the incubated cotyledons by high temperature treatment; milling the boiled cotyledons into a slurry; adding enzyme(s) to the slurry to further enhance hydrolyzing the soy carbohydrates therein and then subsequently deactivating the enzyme; and, deodorizing the cotyledon slurry to form a hydrolyzed soybean base.

The process for formulating the hydrolyzed soybean base may be supplemented with additional steps to create a soy beverage. These additional steps include: mixing sweeteners, stabilization aids, and coloring of the hydrolyzed soybean base; homogenizing the resultant formulated mix; and either sterilizing the homogenized formulation at ultrahigh temperatures for batches to be stored at ambient temperature or pasteurizing the mix at lower temperatures for batches of the homogenized formulation to be refrigerated.

The hydrolyzed soy base manufactured from the process of the present invention has a wide variety of applications. For example, the soy base may be incorporated solely or in combination with dairy or a variety of other food products such as beverages, yogurts, deserts, infant foods, cream liquors, puddings, creams, spreads, cheeses, mayonnaise, sherbets, tofu, yuba, aburrage, milkshakes and soups.

These and other objects, advantages, and features of the invention will be more readily understood and appreciated by reference to the detailed description of the preferred embodiment and the drawings.

DETAILED DESCRIPTION OF THE PREFERRED EMBODIMENT

The present invention can be characterized as a method of manufacturing a soy base from dehulled-whole soybeans partially hydrolyzed with enzymes that may be combined with other ingredients to form a completed soy beverage. The soy base of this invention is an aqueous preparation of the soybean which exhibits: (a) stability of liquid soy base without separation of fat, sedimentation, or coagulation; (b) prolonged storage life; (c) absence of soy flavor; (d) maximum blending capability with fruit juices, fruit juice blends and/or natural or artificial flavors; (e) enhanced compatibility with coloring agents; and (f) increased palatability.

The soymilk of the present invention includes one or more of the following components, all of which are described in detail below: (a) a hydrolyzed soy base made from dehulled-whole soybeans; (b) water; (c) natural or artificial flavoring; (d) natural or artificial sweeteners; (e) stabilization aids; and (f) natural or artificial coloring.

Hydrolyzed Soy Base from Whole Soybeans

The hydrolyzed soy base of the present invention is manufactured from whole soybeans. "Whole soybeans" are any known variety of soybeans with the hull intact. Whole soybeans include an exterior shell, or "hull" that encapsulates the inner portion of the soybean, or the "cotyledon." The "cotyledon" is the portion of the soybean used to produce the hydrolyzed soy base of the present invention. The cotyledon is comprised of a variety of different proteins including mono-, di-, and polypeptides, and sugars, including mono-, di-, and polysaccharides. The cotyledon also includes "endogenous enzymes," which are those enzymes that metabolize proteins and sugars of the cotyledon to promote germination and growth of the soybean plant. Other components and chemicals present in the cotyledon include isoflavones, goitrogens, phytestrogens, Bowman-Birk trypsin inhibitors, saponins, phytates, phosphatides, fiber, fatty acids, vitamins, and minerals.

As will be appreciated by those skilled in the art, the endogenous enzymes include proteinases that, when activated, hydrolyze proteins of the soybean and carbohydrases that, when activated, hydrolyze the carbohydrates of the cotyledons. Another endogenous enzyme present in soybean cotyledons responsible for hydrolysis of fatty acids is the enzyme lipoxygenase which is also heat sensitive. The process for manufacturing the hydrolyzed soy base of the present invention is described in full detail below.

Water

Water contributes to the solubility and stabilization of the hydrolyzed soy base and the completed soy beverage. The water content in the hydrolyzed soy base in one embodiment is at least about 65 percent, in a second embodiment from about 65 percent to about 95 percent, in a third embodiment from about 80 percent to about 90 percent. Parts and percentages are by weight unless otherwise mentioned and temperatures are in degrees Celsius unless otherwise specified.

Additional Components

Sweeteners and stabilization aids may be added to the hydrolyzed soybean base to form a complete soy beverage.

"Sweeteners" include any chemical added to the soy beverage that enhances the sweet taste of the soy beverage. Exemplary sweeteners of a first embodiment of the invention are sucrose and fructose. Sucrose may be added in amounts from about 0% to about 10% in one embodiment, about 1% to about 6% in a second embodiment, and about 3% in a third embodiment. Fructose may be added in addition to or in place of sucrose. Fructose may be added to the soy beverage in amounts from about 0% to about 10% in a first embodiment, from about 1% to about 4% in a second embodiment, or about 2% in a third embodiment. Low calorie or reduced calorie sweeteners may be substituted for sucrose or fructose. Any artificial sweeteners such as aspartame, saccharin and its salts, acesulphame K and glycerrhizinic acid and salts, and their various combinations may also be substituted for or added to the natural sweeteners. The soy beverage can thus be formulated as a product sweetened with natural carbohydrate sweeteners and/or artificial sweeteners.

The flavor of the soy beverage may also be enhanced with flavoring. "Flavoring" refers to any natural or artificial flavoring, or combination thereof. The flavoring may include a variety of flavors including but not limited to strawberry, orange, berry, pineapple, or other fruity flavors. Other flavors such as chocolate, vanilla, etc. may also be used. To further enhance the flavor of the soy beverage, salts, for example, sea salt may be added. Sea salt may be added in amounts from about 0.0% to about 0.01% in a first embodiment, from about 0.0005% to about 0.005% in a second embodiment, and to about 0.001% in a third embodiment.

"Stabilization aids" refer to any substance that tends to keep the soy beverage solution from changing its form, color, or chemical composition. Stabilization aids keep any present pigments and other components in emulsion form and prevent the particles in a colloidal suspension from precipitating. One stabilizing aid is xanthan gum which may be used to keep the water and solids of the soy beverage together in a liquid phase. Xanthan gum may be present in the soy beverage from about 0% to about 0.01% in a first embodiment, from about 0.002% to about 0.008% in a second embodiment, and about 0.005% in a third embodiment. A second stabilization aid used in the soy beverage is lecithin or any derivatives thereof. The lecithin acts as an emulsifier for the oil present in the hydrolyzed soybean base. Lecithin may be present in the soy beverage from about 0.0% to about 0.1%, in another embodiment from about 0.005% to about 0.05%, and in another embodiment about 0.01%. Guar gum, a second suitable stabilization aid, may be present in a first embodiment from about 0.0% to about 0.01%; in a second embodiment from about 0.002% to about 0.008%, and in a third embodiment, about 0.005%. Carboxymethyl cellulose, yet another suitable stabilization aid, may be present in a first embodiment from about 0.0% to about 0.01%; in a second embodiment from about 0.002% to about 0.008%, and in a third embodiment, about 0.005%. As will be appreciated by those skilled in the art, other known stabilization aids may be used as desired.

Manufacture

There will now be described the inventive process used to manufacture the hydrolyzed soy base and completed soy beverage. To begin, whole soybeans are mixed and washed with water in a washing vessel.

Soybean Hydration

The soybeans may be soaked in water having a temperature from about 15° to about 45° C. and a pH of about 6.0 to about 8.0 in a first embodiment, and at the same temperatures but at a pH of about 7.0 in a second embodiment. Depending on the temperature of the water, the time the soybeans are soaked may vary. When describing a temperature over a time period herein as "constant," it is meant that the temperature is maintained continuously at about the given temperature. When describing a temperature as an "inlet" temperature, it is meant that the temperature of the liquid or other substance used is initially added with the specified temperature, however, the temperature may change with time due to cooling or warming of the liquid or substance by ambient conditions. When a temperature is used herein without specifying "inlet" or "constant," the temperature may be considered as either an "inlet" or "constant" temperature.

In one embodiment, soaking in water, or any other suitable liquid, at about a constant 40° C. for about 8 hours is sufficient. In another embodiment, soaking at about a constant 15° C. for about 24 hours is sufficient. In yet another embodiment, soaking at about a constant 35° C. for about 12 hours is sufficient. Accordingly, the soybeans may be soaked in a liquid at a constant temperature of about 40° C. to about 15° C. for about 8 to about 24 hours.

Alternatively, the soybeans may be soaked in an additional embodiment in water having an inlet temperature of about 40° C. for about 12 hours; in another embodiment in water having an inlet temperature of about 35° C. for about 15 hours, and yet another embodiment, in water having an inlet temperature of about 15° C. for about 30 hours. Accordingly, the soybeans may be soaked in water having an inlet temperature of about 40° C. to about 15° C. for about 12 to about 30 hours. During this soaking step, the soybeans are re-hydrated to initiate activation of the endogenous enzymes in the soybeans. After sufficient soaking, the water is removed from the mixing vessel and the partially hydrated soybeans are rinsed in water at about 40° C.

Soybean Incubation

The soybeans are then incubated in a model "L" steam jacketed kettle (BAR, N.A. Inc., Seymour, Ill.) or other comparable steam kettle or incubator, to further activate the endogenous enzymes. In a first process, the soybeans are incubated to about 40° C. for about 10 hours, and may be stirred at least once at the third hour. In another process, the soybeans are incubated at about a constant 35° C. for about 12 hours with the soybeans being stirred, if desired, once at about the 6th hour. In a third process, the soybeans are incubated at about 20° C. constant for about 60 hours and may be stirred, if desired, at about the 30th hour. Accordingly, the soybeans may be soaked at a constant temperature of about 40° C. to about 20° C. for about 10 hours to about 60 hours. The whole soybeans may be incubated at any temperature and duration of time as long as the soybeans are re-hydrated and the proteinases and carbohydrases of the soybean remain enzymatically active.

After incubation, the soybeans may be re-soaked in water in a kettle to re-soften the soybeans at about a constant 50° C. for about one-half hour in a first embodiment; at about a constant 40° C. for about one and a half hours in a second embodiment; and at about a constant 45° C. for about one hour in a third embodiment. Accordingly, the soybeans may be re-soaked in water having a constant temperature of about 50° C. to about 40° C. for about one-half hour to about one and a half hours. After the re-soaking, the water is removed from the steam jacketed kettle, and the soybeans are rinsed with water to reduce the microbial load of the soybeans. In a first embodiment, this water may be at temperatures from about 15° C. to about 50° C. In a second embodiment, the water may be at about 50° C.

Dehulling

Next, the soybeans may be dehulled, that is, their skins are removed from the cotyledons of the whole soybeans. Dehulling reduces the fibrous content of the beans, as the hulls are comprised primarily of fiber. A wet-type model BB soybean dehuller (BAR, N.A., Seymour, Ill.) or other comparable dehuller, may be used to dehull the whole soybeans. The dehuller separates the hulls from the cotyledons and the cotyledons are collected. Alternatively, the soybeans may be extracted using conventional physical or chemical processes as will be appreciated by those skilled in the art.

Protein Hydrolysis

The cotyledons are replaced in the steam jacketed kettle for further incubation. During this step of the process, the soybean proteins are further hydrolyzed. For example, polypeptides, that is, peptide chains having more than ten amino acids, are hydrolyzed to shorter oligopeptides, that is, peptide chains having two to ten amino acids. The cotyledons, in one embodiment, may be incubated at about 45° C. for about 6 hours, in a second embodiment, at about 40° C. for about 8 hours, in a third embodiment, at about 30° C. for about 10 hours, and in a fourth embodiment at about 25° for about 12 hours. Accordingly, the cotyledons are incubated at about 45° C. to about 25° C. for about 6 hours to about 12 hours. Any temperature and duration of incubation is satisfactory as long as the proteinases in the cotyledons are activated to enzymatically assist in the further hydrolysis of soy proteins in the cotyledons. Additional proteinases or enzymes may be added to the cotyledons to enhance protein hydrolysis.

Gelatinization

The protein hydrolyzed cotyledons are then boiled in water for about 25 to about 40 minutes in a first embodiment and about 30 minutes in a second embodiment, in the steam jacketed kettle to induce coagulation and gelatinization of partially hydrolyzed soybeans. "Gelatinization" refers to the formation of a gel or gel-like substance on heating a suspension of polysaccharides or mixtures of polysaccharides and proteins. After boiling, the steam may be turned off. In an alternative embodiment, the cotyledons may be boiled in a solution of food grade buffers, alkali solutions or other solutions as will be appreciated by those skilled in the art, at a temperature of about 65° C. to about 150° C., and a pH of about 6.2 to about 7.5. Examples of suitable food grade buffers are citrate and phosphate; examples of alkali solutions are those including sodium bicarbonate, sodium hydroxide, and/or potassium hydroxide.

Milling

The gelatinized cotyledons may be milled with a model 150 BMI stainless steel mill (BAR N.A. Inc., Seymour, Ill.) or other capable mill. "Milling" means physically breaking down the gelatinized cotyledons into a slurry of small particles.

Polysaccharide Hydrolysis

The cotyledon slurry may be incubated to hydrolyze the carbohydrates, that is, the saccharides in the soybeans. For example, cellulose and hemicellulose (known as polysaccharides) are partially hydrolyzed to beta-glucans and sugars. To enhance the breakdown of the carbohydrates, enzyme(s) is/are added to the cotyledon slurry. Cellulase or a mixture of cellulases is the preferred enzyme, but any other enzyme capable of enhancing the carbohydrate hydrolysis may be used, as will be appreciated by those skilled in the art. In a first embodiment, about 0 to about 10 grams of cellulase per kilogram dry bean weight is added. In another embodiment, about 1 to about 3 grams of cellulase per kilogram dry bean weight is added to the slurry. The slurry is then mixed in one embodiment at a pH of about 6.0 to 7.0, in another embodiment of about 6.0, followed by incubation of the slurry and cellulase enzymes at about 35° to about 55° C. for about 3 hours to about 20 seconds, respectively. The cellulase activity in the slurry may be terminated at the end of incubation by heating the slurry in the kettle to about 90° C. for about ½ hour, followed by cooling the slurry to about 60° C. in the kettle.

Deodorization

The cooled slurry may be deodorized using conventional vacuum pan or evaporator deodorizing processes which will be appreciated by those skilled in the art. Once the slurry is deodorized and concentrated, it may be cooled to about 20° C. This slurry, after the aforementioned processing, is referred to as the "hydrolyzed soybean base." In a first embodiment, the hydrolyzed soy base has a total solids content of about 5% to about 35%, in a second embodiment, about 10% to about 20%, and in a third embodiment, about 15%. The total solids content may vary according to the amount of water that bonds to the polysaccharides, or the variety of whole soybeans used in the process.

Adding Additional Components

The hydrolyzed soybean base may then be mixed in a mixing tank at about room temperature with sweeteners, flavoring, stabilization aids and coloring as desired in a complete soy beverage. Examples of ingredients that may be added include sucrose, fructose, sea salt, xanthan gum, guar gum, lecithin, flavor, and coloring. After all the ingredients are mixed, the formulation may be stirred and stored at about −20° C. to about 60° C. in a first embodiment, at about 0° to about 10° C. in a second embodiment, and at about 4° C. in a third embodiment.

Homogenization

The formulation may be homogenized. "Homogenization" refers to a mechanical process for creating a colloidal system that is unaffected by gravity. In a first embodiment, the formulation may be homogenized from about 4,000 psi to about 30,000 psi. In a second embodiment, the formulation may be homogenized at about 15,000 psi in a Rannie 12.56 VH Homogenizer (APV Americas, Wilmington, Mass.), or other comparable homogenizer. It will be appreciated by those skilled in the art that the higher the pressure, the more smooth and consistent the formulation will become.

Heat Treatment and Bottling

The homogenized formulation may be sterilized and aseptically packaged. "Sterilization" refers to destruction of all bacteria and other infectious organisms in the homogenized formulation or soy beverage. The homogenized formulation may be sterilized in an Armfield FT74DI direct steam injection apparatus, available from Armfield Limited of Hampshire, England, or other comparable sterilizer, at ultra-high temperatures as will be appreciated by those skilled in the art. In the preferred embodiment, the formulation is sterilized at temperature of about 150° C. for about 1 to about 2 seconds in a first embodiment and at about 145° C. for about 5 seconds in a second embodiment. Heat treating at ultra high temperatures for significantly longer periods of time tends to break down the flavoring and coloring of the homogenized formulation. The sterilized homogenized formulation, that is, the resultant soy beverage, may be aseptically packaged to prevent recontamination, in a first embodiment, by hermetic sealing. The sterilized homogenized formulation may be contained in any glass, plastic or other container that is capable of being hermetically sealed. The sterilized homogenized formulation may be stored at room temperature without risk of contamination by bacteria.

The homogenized formulation may alternatively be pasteurized. "Pasteurizing" means killing or inactivating bacterial or other infectious organisms therein. The homogenized formulation may be ultra-pasteurized at about 75° C. to about 99° C. for about one-half hour to about one minute, respectively. The pasteurized homogenized formulation may be stored in any suitable container and then refrigerated.

The resultant soy beverage, that is, either the sterilized homogenized formulation or the pasteurized homogenized formulation, may be consumed in the same manner as known for existing beverages.

EXAMPLE I

A soy beverage manufactured from hydrolyzed dehulled-whole soybeans according to a process of the present invention was analyzed to determine the nutritional values of the beverage. The sample analyzed was 240 ml and included the ingredients in the amounts noted in Table I.

TABLE I

Ingredients of Example 1

| Ingredients | Percent Added |
|---|---|
| Soymilk base solids | 12 |
| Sucrose | 3 |
| Fructose | 2 |
| Sea salt | 0.001 |
| Xantham gum | 0.005 |
| Guar Gum | 0.005 |
| Lecithin | 0.01 |
| Flavor | 0.5 |
| Color | 0.2 |

Table II below sets forth the measured composition of the hydrolyzed beverage as would be required on "nutrition facts" labels for food by the Food & Drug Administration.

TABLE II

Nutritional Facts for Example I

| Nutrient | Amount Per 100 g | Amount Per Serving | % Std. Per Svg |
|---|---|---|---|
| Basic Components | | | |
| Calories | 53 | 129.85 | |
| Protein | 3.36 g | 8.23 g | 16% |
| Carbohydrates | 5.04 g | 12.35 g | 4% |
| Dietary Fiber | 1 g | 2.45 g | 10% |
| Sugar - Total | 4.58 g | 11.22 g | |
| Fat - Total | 2.19 g | 5.37 g | 8% |
| Saturated Fat | 0.31 g | 0.76 g | 4% |
| Cholesterol | 0 mg | 0 mg | 0% |
| Water | 89.09 g | 218.27 g | |
| Ash | 0.32 g | 0.78 g | |
| Calories from Fat | 19.71 | 48.29 | 8% |
| Vitamins | | | |
| Vitamin A IU | 0 IU | 0 IU | 0% |
| Vitamin C | 0 mg | 0 mg | 0% |
| Minerals | | | |
| Calcium | 17 mg | 41.65 mg | 4% |
| Iron | 0.4 mg | 0.98 mg | 5% |
| Sodium | 80 mg | 196 mg | 8% |

Procedure for Manufacture of Example I

Ten kilograms of mixed soybeans were washed twice in 40 liters of water at inlet temperature of 20° C. and rinsed with the same volume of water at 20° C. after each washing. The rinsed soybeans were soaked in 30 liters of water at an inlet temperature of 40° C. at pH 7.0 for 12 hours. The water was drained and the soybeans were rinsed in water at an inlet temperature of 40° C.

The soybeans were placed in a model "L" steam jacketed kettle (BAR, N.A., Inc., Seymour, Ill.) with the lid closed and incubated at a constant 35° C. for 12 hours, with the soybeans being stirred once at the 6th hour. After incubation, the soybeans were re-soaked in water having an inlet temperature of about 50° C. in the kettle for 30 minutes, drained, and rinsed.

The soaked soybeans were dehulled with a wet-type Model BB soybean dehuller at 20° C. and the wet hulls were separated from the cotyledons by the dehuller.

The soybeans were then hydrolyzed at a constant 40° C. for 8 hours in the kettle with the lid closed.

Once incubated, the cotyledons in the incubation water in the steam jacketed kettle were boiled for 30 minutes to induce gelatinization, after which the steam was turned off. The incubation water was not drained.

The boiled cotyledons were milled into a slurry with a model 150 BMI stainless steel mill using the incubation water as mill water. A cellulase enzyme (Genencor, Rochester, N.Y.) was added to the slurry in the kettle in the amount of 1 to 3 grams per kg dry bean weight at a pH of 6.0. Thereafter, the slurry with cellulase was incubated at a constant 50° C. for 1 hour. The cellulase activity in the slurry was terminated by heating the slurry in the kettle to 90° C. for 30 minutes, followed by cooling to 60° C. in the kettle by passing 17° C. inlet temperature water through jacket.

The cooled slurry was transferred to a vacuum pan and evaporated until slurry solids was 15%. The deodorized slurry was pumped into the kettle and cooled with water at 20° C. inlet temperature to form the hydrolyzed soybean base.

The hydrolyzed soybean base was mixed in a mixing tank at 20° C. with the ingredients of Table I above to create a formulation. Once mixed, the formulation was stirred and stored at 4° C. Next, the formulation was homogenized at 15,000 psi in a Rannie 12.56 VH Homogenizer.

A first aliquot of the homogenized formulation was sterilized at 150° C. for 2 seconds in an Armfield FT74DI direct steam injector to produce a sterile soy beverage. The sterile soy beverage was aseptically filled in 330 ml plain glass bottles with rubber-lined caps to hermetically seal the bottles. A second aliquot of the homogenized formulation was pasteurized at 80° C. for 30 minutes and filled into sterile 330 ml plain glass bottles.

The sterilized samples were stored at room temperature of 20° to 22° C., and the pasteurized samples were stored at a refrigerated temperature of about 2° to about 4° C. All samples were observed for signs of instability, specifically coagulation, colloidal separation, sedimentation, or formation of fat and/or whey layering.

Storage Stability

The samples of enzyme-treated dehulled-whole soy beverage that were homogenized at 15,000 psi and sterilized have been under observation for occurrence of coagulation, residue, and formation of whey for 17 months as they are stored at room temperature of about 20° C. The pasteurized samples have been similarly observed for three months as they are stored at about 3°±1° C. No separation of fat, sedimentation, or coagulation has occurred in the sterilized samples or the pasteurized samples.

Consumer Acceptance Tests

Method

An informal population of consumers of about 40 people from ages 18 to 65 were asked to rate the color, aroma, taste, mouthfeel (chalkiness), aftertaste, and detection of soy flavor. The consumers were asked to evaluate the product as highly accepted, accepted, or rejected.

Results

The results of a preliminary consumer test of the stabilized soy beverages are below in Table III.

TABLE III

Preliminary Consumer Acceptance

| Sensory Attribute | Accepted/Rejected |
|---|---|
| Color | Highly accepted |
| Aroma | Highly accepted |
| Taste | Highly accepted |
| Mouthfeel (chalkiness) | Extracted variety (highly accepted) |
| | Dehulled-whole variety homogenized at 4,500 psi (marginally accepted) |
| | Dehulled-whole variety homogenized at 15,000 psi (highly accepted) |
| Aftertaste | No aftertaste (Accepted) |
| Soy flavor | Completely absent (Accepted) |

Additionally, no discernable changes in the sensory attributes of the sterilized sample stored for 17 months occurred when informally tested by consumers.

Based on the above preliminary consumer study, the soy beverage made according to the process of the present invention has sensory attributes that are highly acceptable to consumers. The product also exhibits excellent stabilization to resist aesthetically displeasing coagulation, sedimentation or coagulation that previously required soy beverages to be stored and marketed in opaque containers.

The above descriptions are those of preferred embodiments of the invention. Various alterations and changes can be made without departing from the spirit and broader aspects of the invention as defined in the claims, which are to be interpreted in accordance with the principles of patent law, including the doctrine of equivalents. As used in the specification, the term "includes" or "including" is understood to mean "includes but is not limited to." Except in the claims and the specific examples, or where otherwise expressly indicated, all numerical quantities in this description indicating amounts of material, reaction conditions, use conditions, molecular weights, and/or number of carbon atoms, and the like, are to be understood as modified by the word "about" in describing the broadest scope of the invention. Any reference to an item in the disclosure or to an element in the claim in the singular using the articles "a," "an," "the," or "said" is not to be construed as limiting the item or element to the singular unless expressly so stated. Unless otherwise expressly indicated, all percentages in the claims are weight percentages based on the total weight of the composition. Further, measurements of enzymes in grams are in grams per kilogram dry soybean weight unless otherwise indicated.

The embodiments of the invention in which an exclusive property or privilege is claimed are defined as follows:

1. A method for producing a soybean food base comprising:
   providing whole soybeans that include proteins, carbohydrates, and endogenous enzymes;
   incubating the whole soybeans to activate the endogenous enzymes;
   dehulling the whole soybeans to expose a cotyledon of each of the whole soybeans;
   hydrolyzing the proteins with the endogenous enzyme;
   gelatinizing the cotyledons;
   milling the cotyledons into a slurry; and
   hydrolyzing the carbohydrates with the endogenous enzymes to form a soybean food base.

2. The method of claim 1 wherein the endogenous enzymes include proteinases and cellulases naturally present in the whole soybeans.

3. The method of claim 2 wherein said protein hydrolyzing includes incubating the cotyledons at a temperature and a duration of time sufficient to cause at least one proteinase naturally present in the cotyledons to hydrolyze the proteins in the cotyledons.

4. The method of claim 3 wherein said cotyledons are incubated during said protein hydrolyzing at a temperature of about 45° C. to about 25° C. for about 6 hours to about 12 hours.

5. The method of claim 4 comprising adding a foreign cellulase to the slurry.

6. The method of claim 5 comprising incubating the slurry at a temperature and a duration of time sufficient to activate the added cellulase so that the added cellulase at least partially hydrolyze the carbohydrates in-the slurry.

7. The process of claim 5 comprising adding to the soybean food base ingredients chosen from sweeteners, flavoring, stabilization aids, and coloring.

8. The process of claim 7 comprising homogenizing the soybean food base.

9. The process of claim 8 comprising sterilizing the soybean food base.

10. The process of claim 9 comprising aseptically packaging the soybean food base.

11. The process of claim 8 comprising pasteurizing the soybean food base.

12. The process of claim 1 comprising deodorizing the soybean food base.

13. A process for producing a hydrolyzed soybean base resistant to separation of a colloidal phase and a water phase comprising:
   providing soybean cotyledons including proteins and carbohydrates;
   hydrolyzing the proteins; and
   hydrolyzing the carbohydrates to form a hydrolyzed soybean base containing substantially all the hydrolyzed proteins and the hydrolyzed carbohydrates of the soybean cotyledons, whereby the hydrolyzed proteins and the hydrolyzed carbohydrates are substantially incapable of separating from the water phase.

14. The process of claim 13 comprising breaking down the cotyledons into a slurry.

15. The process of claim 14 wherein proteinases present in the soybean cotyledons hydrolyze the proteins.

16. A process for producing a hydrolyzed soybean base resistant to separation of a colloidal phase and a water phase comprising:
   providing soybean cotyledons including proteins and carbohydrates;
   hydrolyzing the proteins;
   hydrolyzing the carbohydrates, whereby the hydrolyzed proteins and the hydrolyzed carbohydrates are substantially incapable of separating from the water phase; and
   adding an enzyme to the cotyledons to enhance the breakdown of carbohydrates during said carbohydrate hydrolyzing step.

17. The process of claim 16 the enzyme added is cellulase.

18. The process of claim 17 wherein about 0 to about 10 grams of cellulase is added to the slurry.

19. The process of claim 18 comprising deodorizing the hydrolyzed soybean base.

20. The process of claim 18 wherein the cotyledons include at least one proteinase and comprising incubating the slurry at about 45° C. to about 25° C for about 6 hours to about 12 hours to activate the proteinases.

21. The process of claim 20 wherein the cotyledons include at least one carbohydrate hydrolyzing enzyme and comprising incubating the slurry a second time at about 35° C. to about 55° C. for about 3 hours to about 20 seconds to activate the carbohydrate hydrolyzing enzyme in the cotyledons.

22. The process of claim 21 comprising adding to the hydrolyzed soybean base ingredients chosen from sweeteners, flavoring, stabilization aids, and coloring.

23. The process of claim 22 comprising homogenizing the hydrolyzed soybean base.

24. The process of claim 23 comprising sterilizing the hydrolyzed soybean base.

25. The process of claim 24 comprising pasteurizing the hydrolyzed soybean base.

26. The process of claim 14 comprising incorporating the hydrolyzed soybean base into food products chosen from beverages, yogurts, desserts, infant foods, liqueurs, puddings, creams, spreads, cheeses, mayonnaise, sherbets, tofu, yuba, aburrage, milkshakes, and soups.

* * * * *

(12) EX PARTE REEXAMINATION CERTIFICATE (5794th)
United States Patent
Nsofor

(10) Number: US 6,451,359 C1
(45) Certificate Issued: Jun. 26, 2007

(54) SOY BEVERAGE AND RELATED METHOD OF MANUFACTURE

(75) Inventor: Leslie M. Nsofor, Lansing, MI (US)

(73) Assignee: Soy Ultima, L.L.C., East Lansing, MI (US)

Reexamination Request:
No. 90/006,544, Feb. 11, 2003

Reexamination Certificate for:
Patent No.: 6,451,359
Issued: Sep. 17, 2002
Appl. No.: 09/634,933
Filed: Aug. 8, 2000

(51) Int. Cl.
*A23L 1/20* (2006.01)
*A23L 2/38* (2006.01)
*A23J 1/14* (2006.01)

(52) U.S. Cl. .......... 426/46; 426/656; 426/634; 426/598

(58) Field of Classification Search .......... None
See application file for complete search history.

(56) References Cited

U.S. PATENT DOCUMENTS 5,989,600 A 11/1999 Nielsen et al.

6,024,990 A * 2/2000 Kofoed et al. .......... 426/44

FOREIGN PATENT DOCUMENTS

| JP | 59135838 | 8/1984 |
|----|----------|--------|
| JP | 59203462 | 11/1984 |
| JP | 61192256 | 8/1986 |
| JP | 61219347 | 9/1986 |
| JP | 04053460 | 2/1992 |

* cited by examiner

*Primary Examiner*—Dwayne Jones

(57) ABSTRACT

A process for producing a stabilized soy beverage from dehulled whole soybeans partially hydrolyzed with enzymes. The process includes: providing whole soybeans; hydrating the soybeans to activate endogenous enzymes within the soybeans; dehulling the soybeans; hydrolyzing the proteins within the dehulled soybean cotyledons by incubating the cotyledons at elevated temperatures; gelatinizing the incubated cotyledons to induce coagulation of the soybean polysaccharides; milling the gelatinized cotyledons into a slurry; hydrolyzing the polysaccharides of the cotyledons, aided by the addition of cellulase; deodorizing the slurry to form a hydrolyzed soy base; mixing sweeteners, flavoring, and solubilization aids with the hydrolyzed soy base; homogenizing the hydrolyzed soy base; and heat treating the hydrolyzed soy base to form a soy beverage.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 13, 16, 17, 20 and 21 are determined to be patentable as amended.

Claims 2-12, 14, 15, 18, 19 and 22-26, dependent on an amended claim, are determined to be patentable.

1. A method for producing a soybean food base comprising:
   providing whole soybeans that include proteins, carbohydrates, and endogenous enzymes;
   incubating the whole soybeans to activate the endogenous enzymes;
   dehulling the whole soybeans to expose a cotyledon of each of the whole soybeans;
   [hydrolyzing] *incubating the cotyledons to hydrolyze* the proteins with the endogenous [enzyme] *enzymes*;
   gelatinizing the cotyledons;
   milling the cotyledons into a slurry;
   *adding a foreign enzyme to the slurry*; and
   [hydrolyzing] *incubating the slurry to hydrolyze* the carbohydrates with the [endogenous enzymes] *foreign enzyme* to form a soybean food base, *wherein the slurry incubating, carbohydrate hydrolyzing step is performed after the whole soybean incubating, protein hydrolyzing step to prevent sedimentation of at least one of the proteins and carbohydrates.*

13. A process for producing a hydrolyzed soybean base resistant to separation of a colloidal phase and a water phase comprising:
    providing soybean cotyledons including proteins and carbohydrates;
    [hydrolyzing] *incubating the cotyledons at a first temperature to hydrolyze* the proteins; and
    [hydrolyzing] *re-incubating the cotyledons at a second temperature greater than the first temperature to hydrolyze* the carbohydrates to form a hydrolyzed soybean base containing substantially all the hydrolyzed proteins and the hydrolyzed carbohydrates of the soybean cotyledons, [whereby] *wherein the re-incubating, carbohydrate hydrolyzing step is carried out after the incubating, protein hydrolyzing step to render* the hydrolyzed proteins and the hydrolyzed carbohydrates [are] substantially incapable of separating from the water phase *and to prevent formation of a sediment.*

16. A process for producing a hydrolyzed soybean base resistant to separation of a colloidal phase and a water phase comprising:
    providing soybean cotyledons including proteins[and], carbohydrates *and endogenous enzymes*;
    *hydrating the soybean cotyledons to initiate activation of the endogenous enzymes;*
    hydrolyzing the proteins *by incubating the soybeans*; and
    hydrolyzing the carbohydrates[, whereby] *in a separate step after the protein hydrolyzing step by re-incubating the soybeans so that* the hydrolyzed proteins and the hydrolyzed carbohydrates are substantially incapable of separating from the water phase[;] and
    [adding an enzyme to the cotyledons to enhance the breakdown of carbohydrates during said carbohydrate hydrolyzing step.] *unable to form a sediment.*

17. The process of claim 16 *comprising adding an enzyme to the cotyledons to enhance the breakdown of carbohydrates during said carbohydrate hydrolyzing step, wherein* the enzyme added is cellulase.

20. The process of claim 18 wherein the cotyledons include at least one proteinase [and comprising incubating the slurry], *wherein the incubating is performed* at about 45° C. to about 25° C. for about 6 hours to about 12 hours to activate the proteinases.

21. The process of claim 20 wherein the cotyledons include at least one carbohydrate hydrolyzing enzyme [and comprising incubating the slurry a second time], *wherein the re-incubating is performed* at about 35° C. to about 55° C. for about 3 hours to about 20 seconds to activate the carbohydrate hydrolyzing enzyme in the cotyledons.

\* \* \* \* \*